United States Patent [19]

Röder

[11] 4,454,227

[45] Jun. 12, 1984

[54] METHOD FOR CULTIVATING INSECT CELLS

[75] Inventor: Anton Röder, Kelkheim, Fed. Rep. of Germany

[73] Assignee: Hoechst Aktiengesellschaft, Frankfurt am Main, Fed. Rep. of Germany

[21] Appl. No.: 332,196

[22] Filed: Dec. 18, 1981

[30] Foreign Application Priority Data

Dec. 20, 1980 [DE] Fed. Rep. of Germany ....... 3048289

[51] Int. Cl.$^3$ .......................... C12N 5/00; C12N 1/38; C12N 5/02; C12R 1/91
[52] U.S. Cl. .................................... 435/240; 435/244; 435/241; 435/948
[58] Field of Search ...................... 435/1, 2, 240, 241, 435/244, 948

[56] References Cited

U.S. PATENT DOCUMENTS 2,598,881  6/1952  Berliner ................................. 435/2
4,072,570  2/1978  Williams ................................ 435/2

FOREIGN PATENT DOCUMENTS 0604556  4/1978  U.S.S.R. ................................ 435/2

OTHER PUBLICATIONS

Eylan et al., "Biological Characteristics of a Stimulatory Factor for Viral Replication Detected in Egg Fluids," Archives of Virology 56 (1-2), (1978), pp. 47-59, Chem. Abst. 88: 100684m.

Stadelman et al., "Egg Science and Technology", 2nd edition, AVI Publishing Co., Inc., Westport, Conn., (1977), pp. 279-280.

"Difco Manual", Ninth Edition, (1954), Difco Laboratories, Detroit, MI.

Mitsuhashi, "Culture Media for Invertebrate Embryos", CRC Handbook Series in Nutrition and Food, vol. IV, (1977), pp. 241-243.

Jakoby et al., "Cell Culture", Methods in Enzymology, vol. 58, (1979), pp. 454-457.

Yunker et al., "Adaptation of an Insect Cell Line (Grace's Antheraea Cells) to Medium Free of Insect Hemolymph", Science, vol. 155, (1967), pp. 1565-1566.

Vaughn, "Insect Cells for Insect Virus Production", Advances in Cell Culture, vol. 1, (1981), pp. 281-295.

Stanley, "Cultivation of Arthropod Cells" in Growth, Nutrition and Metabolism of Cells in Culture, by Rothblat et al., (1972), pp. 331-333.

Gardiner et al., J. Invertebrate Pathology 25, 363-70, (1975).

Primary Examiner—Thomas G. Wiseman
Assistant Examiner—John E. Tarcza
Attorney, Agent, or Firm—Curtis, Morris & Safford

[57] ABSTRACT

Cultivation and reproduction of insect cells in a nutrient medium in which fetal calf serum is partially or completely replaced by egg yolk.

6 Claims, No Drawings

METHOD FOR CULTIVATING INSECT CELLS

In connection with the general discussion on the environmental hazard of chemical pesticides, biological methods for combating pests have gathered momentum. One of the most promising methods is the use of highly specific insect pathogenic viruses, especially nucleopolyhedrosis viruses (NPV) and granulosis viruses (GV) from the group of baculoviruses. These viruses are applied to the environment in the same manner as chemical pesticides, where they are picked up by their specific hosts in which they cause a virus infection killing the hosts within a short period of time. A number of NPV and GV products are already commercialized or are tested for practical use (see Shieh and Bohmfalk, Production and Efficiency of Baculoviruses, Biotechnology and Bioengineering Vol. XXII, 1357 et seq. (1980)).

However, the production of sufficient quantities of virus material meets with practical problems which have not found a satisfactory solution as yet. In principle, there are two methods available (loc. cit., 1361 et seq.):

(1) reproduction of large host numbers, artificial infection with virus and isolation of virus from the dead animals;

(2) cultivation of individual insect cells in vitro in a suitable nutrient medium, infection of the cells and work-up of the virus material.

The method described, sub (1), although supplying large amounts of virus material, has the following disadvantages: the host animals are available only during a limited period of the year, and the virus material is contaminated with insect residues and microbial impurities. Although purification is possible, it would greatly raise the cost of production.

The method described sub (2) avoids these difficulties; however, it depends fully on the availability of a suitable culture medium. The compositions proposed or used for this purpose contain, in addition to inorganic salts, vitamins, amino acids, sugars and a number of other organic compounds important for cell physiology, about 5 to 20% of fetal calf serum (FCS) which is indispensable for cell growth. Typical compositions are for example described in Nature 195, 4843 (1962) and J. Invertebrate Pathology 25, 363-370 (1975).

FCS is the limiting factor due to its high price and because it is available in relatively small amounts only. Production of insect cells on an industrial scale required for an industrial manufacture of insect pathogenic viruses is therefore not possible in this way. There is thus the need of replacing FCS by a cheaper component available in sufficient quantities.

Surprisingly, it has now been found that instead of FCS, egg yolk can be advantageously used.

Subject of the invention is therefore a method for cultivation and reproduction of cells, especially insect cells, with the use of known nutrient media containing inorganic salts, amino acids, sugars, vitamins and other organic substances, which comprises adding egg yolk to these nutrient media.

The content of egg yolk is from 0.1 to 5, preferably 0.5 to 2, % by weight of the nutrient solution. It may replace FCS completely or partially.

For preparing a nutrient medium suitable for cell culture, only about 5 to 20% of the FCS amount of egg yolk is required. The egg yolk must not necessarily be separated from the egg white; suitable are therefore also whisked eggs, for example. Preferably, however, commercial egg yolk emulsion is used.

The origin of the egg yolk, too, is of secondary importance only. For reasons of availability, egg yolk of hen's eggs is particularly suitable, but duck and goose eggs may also be used as source of egg yolk.

The method of the invention is suitable for the cultivation of numerous insect cell lines, for example from the orders of diptera and lepidoptera. There may be mentioned for example cell lines of *Spodoptera frugiperda, Lymantria dispar, Mamestra brassicae, Trichoplusia ni, Aedes albopictus* and *Aedes aegypti,* which in turn are suitable for the reproduction of numerous insect-pathogenic viruses such as parvoviruses, pox viruses, baculoviruses and rhabdoviruses, of which especially nucleopolyhedrosis viruses such as those from Autographa spp., Spodoptera spp. and Lymantria spp. are of interest.

The process is subsequently described using the cultivation of an established cell strain of *Spodoptera frugiperda* (Sf) as example.

To a commercial TC 10 culture medium (consisting of a salt solution, glucose, defined amounts of amino acids and vitamins and a protein hydrolysate (tryptose broth)) 5% by weight of FCS (instead of the usual 10%) and 0.5% by weight of commercial egg yolk emulsion were added. In the culture medium thus modified the cells were cultivated using monolayer flasks (3 ml), shaker cultures (20 ml) and flasks with stirrer (500 ml). The addition of egg yolk increased the cell yield by 100% (from $1.4 \times 10^6$ to $2.8 \times 10^6$ cells/ml) as compared with a control batch containing 10% of FCS only.

In further tests, FCS was completely omitted and varying egg yolk concentrations were used. At a rate of 1% of egg yolk FCS could be completely replaced; the cell yield was in the same range as that obtained when using 10% of FCS (Table 1).

TABLE 1

| Cell yield at addition of FCS or egg yolk emulsion in monolayer system after 50 passages | | |
|---|---|---|
| | cell yield (cells/ml) on use of TC 10 | |
| | + 10% FCS | + 1% egg yolk emulsion |
| Test 1 | $1.4 \times 10^6$ | $1.4 \times 10^6$ |
| Test 2 | $2.0 \times 10^6$ | $1.7 \times 10^6$ |
| Test 3 | $1.4 \times 10^6$ | $1.8 \times 10^6$ |

Comparable results were obtained when cultivating the cells in shaked or stirred solutions. Long duration tests proved that the cell growth in the culture media of the invention was stable over more than 60 passages.

The cells cultivated in a FCS-free medium with addition of egg yolk were regularly used as substrate for the production of insect pathogenic nucleopolyhedrosis viruses. The virus yield remained unchanged as compared to control batches with addition of FCS (Table 2).

TABLE 2

| Polyhedrosis virus yield in monolayer system | | |
|---|---|---|
| | TC 10 | |
| | + 10% CFS | + 1% egg yolk |
| PIB/ml (polyhedral inclusion bodies) | $1.3 \times 10^7$ $1.9 \times 10^7$ | $1.2 \times 10^7$ $1.6 \times 10^7$ $1.3 \times 10^7$ |

TABLE 2-continued

| Polyhedrosis virus yield in monolayer system | |
|---|---|
| TC 10 | |
| + 10% CFS | + 1% egg yolk |
| (2 tests) | (3 tests) |

Electron-optical examinations and infection tests in vitro proved that the morphology and the biological activity of the viruses produced were unchanged.

What is claimed is:

1. In a method which comprises cultivating and reproducing insect cells in a nutrient medium containing inorganic salts, amino acids, sugars and vitamins, the improvement which comprises adding unmodified poultry egg yolk to the nutrient medium.

2. The method defined in claim 1, wherein said nutrient medium further contains fetal calf serum (FCS).

3. The method defined in claim 2 in which the concentration of poultry egg yolk is from 0.1 to 5 weight % relative to the nutrient medium.

4. The method defined in claim 3, wherein the concentration of poultry egg yolk is from 0.5 to 2 weight %.

5. The method defined in claim 1 in which the concentration of poultry egg yolk is from 0.1 to 5 weight % relative to the nutrient medium.

6. The method defined in claim 5, wherein the concentration of poultry egg yolk is from 0.5 to 2 weight %.

* * * * *